United States Patent
Kawasaki et al.

(10) Patent No.: US 12,397,075 B2
(45) Date of Patent: Aug. 26, 2025

(54) PASS BOX

(71) Applicant: AIREX CO., LTD., Nagoya (JP)

(72) Inventors: Koji Kawasaki, Nagoya (JP); Daisuke Kakuda, Nagoya (JP); Jun Masudome, NNagoya (JP); Tsukasa Kitano, Nagoya (JP); Zhiqiang Guo, Nagoya (JP)

(73) Assignee: AIREX CO., LTD, Nagoya (JP)

( * ) Notice: Subject to any disclaimer, the term of this patent is extended or adjusted under 35 U.S.C. 154(b) by 919 days.

(21) Appl. No.: 17/601,665

(22) PCT Filed: Mar. 18, 2020

(86) PCT No.: PCT/JP2020/011924
§ 371 (c)(1),
(2) Date: Mar. 4, 2022

(87) PCT Pub. No.: WO2020/230449
PCT Pub. Date: Nov. 19, 2020

(65) Prior Publication Data
US 2022/0193291 A1     Jun. 23, 2022

(30) Foreign Application Priority Data
May 14, 2019   (JP) ................................ 2019-091088

(51) Int. Cl.
*A61L 2/22*     (2006.01)

(52) U.S. Cl.
CPC ........... *A61L 2/22* (2013.01); *A61L 2202/122* (2013.01); *A61L 2202/14* (2013.01); *A61L 2202/15* (2013.01)

(58) Field of Classification Search
CPC ............................. A61L 2/22; A61L 2202/122
See application file for complete search history.

(56) References Cited

U.S. PATENT DOCUMENTS

2013/0183749 A1*   7/2013   Aamodt .................... A61L 9/14
                                                                        435/287.1
2015/0191766 A1*   7/2015   Kobayashi .............. A61L 2/186
                                                                        435/309.1

(Continued)

FOREIGN PATENT DOCUMENTS

| CN | 109570109 A | * | 4/2019 |
| JP | H01178041 U | | 12/1989 |

(Continued)

OTHER PUBLICATIONS

PCT International Search Report, PCT/JP2020/011924, Jun. 9, 2020, 6 pages.

*Primary Examiner* — Michael A Marcheschi
*Assistant Examiner* — Kayla Rose Sarantakos
(74) *Attorney, Agent, or Firm* — Quarles & Brady LLP; Yakov S. Sidorin (57) ABSTRACT

A pass box configured to accommodate and decontaminate an article by concentrating a mist of decontamination agent on an article's surface and to reduce a duration of aeration operations. The box includes a decontamination chamber, an aeration chamber in which residue of the decontamination agent is removed from the article's surface, a decontamination agent supply device, a decontamination agent control device, a moving device configured to reposition the article, and an air supply and exhaust device. The decontamination agent supply device converts a chemical into the mist and supplies it into the decontamination chamber. The decontamination agent control device includes vibration boards that are adjacent to internal wall surfaces of the decontamination chamber and that are ultrasonically vibrated to generate sound flows in the vertical direction thereby pressing the mist with acoustic radiation to concentrate the mist on the external surfaces of the article.

16 Claims, 5 Drawing Sheets

(56) References Cited

U.S. PATENT DOCUMENTS

2015/0239020 A1* 8/2015 Ponomarev ............. B08B 7/028
                                                    134/1
2018/0099259 A1* 4/2018 Kawasaki ............ B01D 49/006

FOREIGN PATENT DOCUMENTS

| JP | 2004537345 A | 12/2004 |
| JP | 2006198120 A | 8/2006 |
| JP | 2008253937 A | 10/2008 |
| JP | 2009195563 A | 9/2009 |
| JP | 2012029859 A | 2/2012 |
| JP | 2012061403 A | 3/2012 |

* cited by examiner

PASS BOX

CROSS-REFERENCE TO RELATED APPLICATIONS

This application represents the US national stage entry from the International Application No. PCT/JP2020/011924, filed on Mar. 18, 2020, that claims priority from the Japanese Patent Application No. JP 2019-091088 filed on May 14, 2019. The disclosure of each of the above-identified patent documents is incorporated by reference herein.

TECHNICAL FIELD

The present invention relates to a pass box associated with sterile environmental chambers such as an isolator and, more particularly, to a pass box capable of efficiently decontaminating an article conveyed to these sterile areas.

RELATED ART

In manufacturing settings for pharmaceutical products and so forth, the indoor working area must inevitably be kept sterile. Particularly in cases where clean rooms (such as, for example, a working chamber for manufacturing pharmaceutical products) are decontaminated, advanced decontamination validation needs to be accomplished in accordance with Good Manufacturing Practice (GMP).

The recent advanced technology in the field of regenerative medicine has led to wide use of incubators for cell culture. Such cell-based regenerative medicine techniques require steps for controlling, culturing and processing collected cells (Cell Processing), which are performed in plants referred to as "Cell Processing Center" (CPC). The CPC employs isolators as a working chamber that requires the highest cleanliness of grade A.

A small chamber is employed as an isolator that allows an operator to work through gloves or a half-suit from the outside of the chamber. The isolator chamber is provided with an intake and exhaust device for maintaining a sterile state so as to receive no contaminants from the external environment. In addition, a sterile state is intended to be maintained when necessary equipment and articles are conveyed to the inside of an isolator in the sterile state from the external environment.

For example, a small spare chamber for conveying, referred to as a "pass box", is provided for an article to be conveyed to the inside of the isolator. An operator, who will convey an article to the inside of the isolator, first conveys the article to a pass box. In this case, a carry-in door between the isolator and the pass box is sealed. Subsequently, the carry-in door between the pass box and the external environment is sealed to decontaminate the article together with the inside of the pass box. After the pass box is completely decontaminated and a gas for decontamination or the like is removed, the carry-in door between the isolator and the pass box is opened to convey the article to the inside of the isolator.

In recent years, hydrogen peroxide has widely been used (in the form of a in the form of a gas or mist) to decontaminate a working chamber such as an isolator and a pass box (hereinafter referred to as a "room to be decontaminated") and articles to be conveyed. Advantageously, hydrogen peroxide has a strong sterilization effect, and is inexpensively available and effectively utilized as an environmentally-friendly decontamination agent that is ultimately resolved into oxygen and water.

In decontamination operations by hydrogen peroxide, a log spore reduction (LRD) value calculated by the logarithmic decrement of fungi can be 4 to 6 or more, indicating a sufficiently acceptable decontamination standard effect. Unfortunately, a decontamination work by hydrogen peroxide needs long duration of 45- to 120-minute operations including an aeration operation for removing hydrogen peroxide that is residual on an article or inside a pass box in the state of a condensed film or the like after decontamination, in addition to a decontamination operation.

The following Patent Document 1 proposes a cell treatment device that employs no decontamination approaches by hydrogen peroxide in the field of regenerative medicine where articles are frequently conveyed to an isolator with the cleanliness maintained at grade A. The cell treatment device serially connects at two stages a pass box to an isolator of grade A. In the isolator and the pass box, the air pressure controls the air flow direction.

First, at the first stage in the pass box to which an article has been conveyed from the external environment, an operator in the external environment decontaminates using gloves external surfaces of the article (a packaging bag that accommodates a sterilized container) by wiping out the same with an alcohol-containing cloth. Subsequently, the operator conveys the decontaminated packaging bag to the second stage in the pass box, and takes containers out of the packaging bag. Then, the containers are conveyed to the isolator of grade A.

CITATION LIST

Patent Literature

Patent Document 1: WO-2017-069147 A

SUMMARY OF THE INVENTION

Technical Problem

In fact, the invention in the above Paten Document 1 achieves shorter-time decontamination operations than conventional hydrogen peroxide-based techniques. Nevertheless, medical GMP standards fail to constantly assure an LRD value of 4 to 6 capable of achieving the grade A conveying environment. In addition, when the air pressure in the pass box is controlled, advanced control, such as air pressure cascade control, cannot readily be performed in such a small space. Therefore, shorter-time decontamination has been desired using conventionally widely used and highly reliable hydrogen peroxide.

Thus, the present invention was made in view of the situation to solve the problems, and has an object to provide a pass box capable of accomplishing a decontamination effect with a proper amount of decontamination agent by concentrating a mist for decontamination on the surface of an article to be conveyed to grade A environment, and of achieving more efficient decontamination works by reducing the duration of aeration operations.

Solution to the Problem

To solve the aforementioned problem, inventors of the present invention have carried out an extended investigation to find that a pass box is divided into a decontamination chamber and an aeration chamber, a hydrogen peroxide mist supplied to the pass box is miniaturized by employing ultrasonic vibration in a decontamination agent control device, and the hydrogen peroxide mist is allowed to concentrate on the surface of an article in the pass box. Based on that technique, the present invention was accomplished.

Specifically, a pass box according to the present invention includes, according to recitation in claim 1,
- a pass box (100) used for conveying an article (P) to the inside of a working chamber or to a location outside the pass box with a sterile environment maintained, including
- a first chamber (30) for decontaminating external surfaces of the article with a decontamination agent, a second chamber (20) for removing the decontamination agent that is residual on the external surfaces of the decontaminated article, a decontamination agent supply device (70) for supplying a decontamination agent, a decontamination agent control device (60) for controlling the movement of the supplied decontamination agent, a moving device (50) for moving or repositioning the article, and an air supply and exhaust device for supplying and exhausting clean air, characterized in that
- the first chamber includes a first door (31) for conveying an article to the inside from the external environment, a supply port of the decontamination agent supply device, and an exhaust port (34) of the air supply and exhaust device,
- the second chamber includes a second door (25) provided on the boundary with the first chamber, a third door (21) for conveying the aerated article to the inside of the working chamber or to a location outside the pass box, and a supply port (23) of the air supply and exhaust device,
- the decontamination agent supply device converts a chemical for decontamination into a mist for decontamination (M2), and supplies the same to the inside of the first chamber that accommodates the article through the supply port,
- the decontamination agent control device includes vibration boards (61, 62) disposed adjacent to internal wall surfaces of the first chamber, the vibration boards ultrasonically vibrate to generate sound flows (61b, 62b) from board surfaces (61a, 62a) by an ultrasound in the vertical direction, and the mist for decontamination supplied to the first chamber is pressed by acoustic radiation pressure to concentrate the mist for decontamination on the external surfaces of the article,
- the moving device moves/reposition the decontaminated article from the first chamber to the second chamber, and
- the air supply and exhaust device performs aeration for removing the decontamination agent that is residual on the external surfaces of the article by supplying clean air to the second chamber through the supply port, and discharges the air containing the aerated decontamination agent into the external environment through the exhaust port.

Furthermore, the present invention includes, according to description in claim 2, the pass box according to claim 1, characterized in that
- the second chamber is located above the first chamber, the air supply and exhaust device is disposed such that a supply port thereof is open at an upper portion of the second chamber and an exhaust port thereof is open at a lower portion of the first chamber, characterized in that
- the clean air supplied from the air supply and exhaust device to the second chamber is converted into a unidirectional flow from the upper to lower portions of the first chamber through the external surfaces of the article from the upper portion of the second chamber, and discharged from the exhaust port that is open at the lower portion of the first chamber into the external environment while the external surfaces of the article and the inside of the first chamber are aerated when the article is in the second chamber for aeration.

Moreover, the present invention includes, according to description in claim 3, the pass box according to claim 1 or 2, characterized in that
- the decontamination agent control device includes a plurality of vibration boards, characterized in that
- the plurality of vibration boards is arranged with the article in the first chamber placed therebetween and board surfaces thereof being opposite each other, and the resulting pressing force by the acoustic radiation pressure primarily concentrates in the direction of the article from each of the vibration boards, and
- the mist for decontamination is controlled to concentrate on the external surfaces of the article.

Furthermore, the present invention includes, according to description in claim 4, the pass box according to claim 1 or 2, characterized in that
- the decontamination agent control device includes a plurality of vibration boards, characterized in that
- the plurality of vibration boards is arranged with the article in the first chamber placed therebetween and without board surfaces thereof being opposite each other, and the resulting pressing force by the acoustic radiation pressure primarily passes along a side surface of the article from each of the vibration boards, and
- the mist for decontamination is controlled to concentrate on the external surfaces of the article by moving so as to rotate inside the first chamber.

Moreover, the embodiment of the present invention includes, according to description in claim 5, the pass box according to any one of claims 1 to 4, characterized in that
- the decontamination agent supply device includes a mist generation means, characterized in that
- the mist generation means is a spray nozzle such as a single-fluid nozzle or a two-fluid nozzle, or an ultrasonic mist generator such as an ultrasonic humidifier, a nebulizer or a piezo atomizer, and
- a primary mist of the decontamination agent generated by the mist generation means is supplied to the first chamber as a mist for decontamination through the supply port of the decontamination agent supply device included in the first chamber.

Furthermore, the present invention is, according to description in claim 6, the pass box according to claim 5, characterized in that
- the decontamination agent supply device includes a mist microparticulating means (73), characterized in that
- the mist microparticulating means includes one or more vibration boards (73a, 73b), and the vibration boards ultrasonically vibrate to generate sound flows (73e, 73f) from board surfaces (73c, 73d) by an ultrasound in the vertical,
- the primary mist (M1) of the decontamination agent generated by the mist generation means is subjected to ultrasonic vibration by the sound flows to further miniaturize the primary mist into a secondary mist (M2), and
- the generated secondary mist is supplied to the first chamber as a miniaturized mist for decontamination through the supply port of the decontamination agent supply device included in the first chamber.

Moreover, the present invention includes, according to description in claim 7, the pass box according to any one of claims 1 to 6, characterized in that the second chamber includes one or more vibration boards (328) disposed adjacent to internal wall surfaces thereof, the vibration boards ultrasonically vibrate to generate sound flows (328*b*) from board surfaces (328*a*) by an ultrasound in the vertical direction, and the decontamination agent that is residual on the surface of the article is removed by allowing the clean air and the sound flow to act on the external surfaces of the decontaminated article to be aerated in the second chamber.

Furthermore, the present invention includes, according to description in claim 8, the pass box according to any one of claims 1 to 7, characterized in that the vibration board includes a base (61*c*) and a plurality of transmitters (61*e*), characterized in that the plurality of transmitters is arranged on a planar surface of the base so as to be uniform in transmission directions, and the transmitters are operated in the same phase, whereby a sound flow is generated by a significantly directional ultrasound from the board surface of the vibration board in the vertical direction by mutually amplifying the ultrasounds of the plurality of transmitters in the front direction and mutually canceling out the ultrasounds of the plurality of transmitters in the lateral direction.

Moreover, the embodiment of the present invention includes, according to description in claim 9, the pass box according to any one of claims 1 to 8, characterized in that the mist for decontamination supplied to the inside of the working chamber is further miniaturized by ultrasonic vibration generated from the vibration board.

Furthermore, the embodiment of the present invention includes, according to description in claim 10, the pass box according to any one of claims 1 to 9, including a control device for changing the frequency and output of the ultrasound generated from the vibration board and/or for transmitting an ultrasound intermittently to control the position or moving speed of the mist for decontamination controlled to concentrate on the external surfaces of the article.

Advantageous Effects of the Invention

According to the above configuration, the pass box of the present invention is used for conveying an article to the inside of a working chamber or to a location outside the pass box where the sterile environment is maintained, including a first chamber for decontaminating external surfaces of the article with a decontamination agent, a second chamber for removing the decontamination agent that is residual on the external surfaces of the decontaminated article, a decontamination agent supply device for supplying a decontamination agent, a decontamination agent control device for controlling the movement of the supplied decontamination agent, a moving device for moving the article, and an air supply and exhaust device for supplying and exhausting clean air.

The first chamber includes a first door for conveying an article to the inside from the external environment, a supply port of the decontamination agent supply device, and an exhaust port of the air supply and exhaust device. The second chamber includes a second door provided on the boundary with the first chamber, a third door for conveying the aerated article to the inside of the working chamber or to a chosen location outside the pass box, and a supply port of the air supply and exhaust device. The decontamination agent supply device converts a chemical for decontamination into a mist for decontamination, and supplies the same to the inside of the first chamber that accommodates the article through the supply port. The decontamination agent control device includes vibration boards disposed adjacent to internal wall surfaces of the first chamber, the vibration boards ultrasonically vibrate to generate sound flows from board surfaces by an ultrasound in the vertical direction, and the mist for decontamination supplied to the first chamber is pressed by acoustic radiation pressure to concentrate the mist for decontamination on the external surfaces of the article. The moving device repositions the decontaminated article from the first chamber to the second chamber. The air supply and exhaust device performs aeration for removing the decontamination agent that is residual on the external surfaces of the article by supplying clean air to the second chamber through the supply port, and discharges the air containing the aerated decontamination agent into the external environment through the exhaust port.

Thus, according to the above configuration, the present invention can provide a pass box capable of accomplishing a decontamination effect with a proper amount of decontamination agent by concentrating a mist for decontamination on the surface of an article to be conveyed to grade A environment, and of achieving more efficient decontamination works by reducing the duration of aeration operations.

According to the above configuration, the second chamber is located above the first chamber. The air supply and exhaust device is disposed such that a supply port thereof is open at an upper portion of the second chamber and an exhaust port thereof is open at a lower portion of the first chamber. Accordingly, the clean air supplied from the air supply and exhaust device to the second chamber is converted into a unidirectional flow from the upper to lower portions of the first chamber through the external surfaces of the article from the upper portion of the second chamber and the second door, and discharged from the exhaust port that is open at the lower portion of the first chamber into the external environment while the external surfaces of the article and the inside of the first chamber are aerated when the article is in the second chamber for aeration. Thus, the above operational advantage can more specifically be provided.

According to the above configuration, the decontamination agent control device includes a plurality of vibration boards, these vibration boards are arranged with the article in the first chamber placed therebetween and board surfaces thereof being opposite each other, and the resulting pressing force by the acoustic radiation pressure primarily concentrates in the direction of the article from each of the vibration boards. Accordingly, the mist for decontamination is controlled to concentrate on the external surfaces of the article. Thus, the above operational advantage can more specifically be provided.

According to the above configuration, the decontamination agent control device includes a plurality of vibration boards, these vibration boards are arranged with the article in the first chamber placed therebetween and without board surfaces thereof being opposite each other, and the resulting pressing force by the acoustic radiation pressure primarily passes along a side surface of the article from each of the vibration boards. Accordingly, the mist for decontamination is controlled to concentrate on the external surfaces of the article by moving so as to rotate inside the first chamber. Thus, the above operational advantage can more specifically be provided.

According to the above configuration, the decontamination agent supply device includes a mist generation means. The mist generation means is a spray nozzle such as a single-fluid nozzle or a two-fluid nozzle, or an ultrasonic mist generator such as an ultrasonic humidifier, a nebulizer or a piezo atomizer. Accordingly, the decontamination agent supply device supplies a primary mist of the decontamination agent generated by the mist generation means to the first chamber as a mist for decontamination through the supply port of the decontamination agent supply device included in the first chamber. Thus, the above operational advantage can more specifically be provided.

According to the above configuration, the decontamination agent supply device includes a mist microparticulating means, in addition to the mist generation means. The mist microparticulating means includes one or more vibration boards, and the vibration boards ultrasonically vibrate to generate sound flows from board surfaces by an ultrasound in the vertical direction. The primary mist of the decontamination agent generated by the mist generation means is subjected to ultrasonic vibration by the sound flows to further miniaturize or reduce in size the primary mist into a secondary mist that has smaller dimensions. Accordingly, the generated secondary mist is supplied to the first chamber as a miniaturized mist for decontamination through the supply port of the decontamination agent supply device included in the first chamber. Thus, the above operational advantage can more specifically be provided.

According to the above configuration, the second chamber includes one or more vibration boards disposed adjacent to internal wall surfaces thereof, the vibration boards ultrasonically vibrate to generate sound flows from board surfaces by an ultrasound in the vertical direction. Accordingly, the decontamination agent that is residual on the surface of the article is removed by allowing the clean air and the sound flow to act on the external surfaces of the decontaminated article to be aerated in the second chamber; in the second chamber, therefore, the decontaminated article is turned into an aerated article. Thus, the above operational advantage can more specifically be provided.

According to the above configuration, the vibration board includes a base and a plurality of transmitters, and the plurality of transmitters is arranged on a plain surface of the base so as to be uniform in transmission directions, and the transmitters are operated in the same phase. Accordingly, a sound flow is generated by a significantly directional ultrasound from the board surface of the vibration board in the vertical direction by mutually amplifying the ultrasounds of the plurality of transmitters in the front direction and mutually canceling out the ultrasounds of the plurality of transmitters in the lateral direction. Thus, the above operational advantage can more specifically be provided.

According to the above configuration, the mist for decontamination supplied to the inside of the working chamber is further miniaturized by ultrasonic vibration generated from the vibration board. Thus, the above operational advantage can more specifically be provided.

According to the above configuration, the pass box may include a control device for changing the frequency and output of the ultrasound generated from the vibration board and/or for transmitting an ultrasound intermittently. Accordingly, the position or moving speed of the mist for decontamination controlled to concentrate on the external surfaces of the article is controlled. Thus, the above operational advantage can more specifically be provided.

DETAILED DESCRIPTION

According to the idea of the present invention, a liquid decontamination agent or a decontamination agent solution is allowed to act on an article to be decontaminated in the form of mist. Herein, "mist" is broadly interpreted as the state of a liquid droplet of a decontamination agent miniaturized and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the mist according to the present invention is categorized into a "mist" (the size may be defined as 10 μm or less) or a "fog" (the size may be defined as 5 μm or less), and a mist having a larger particle size. In the present invention, ultrasonic vibration converts even a mist, a fog and a liquid droplet sized 3 to 10 μm or more into equalized ultrafine particles 3 μm or less to provide high-level decontamination effects (later-described).

The pass box according to the present invention will be described with reference to each of the embodiments. The present invention is not restricted to each of the following embodiments.

First Embodiment

Figure 1:
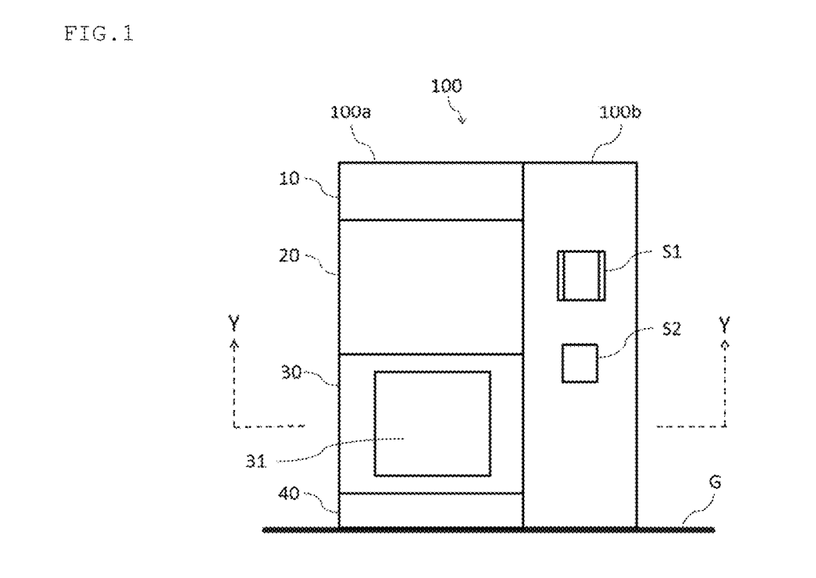
FIG. 1 is a front view of a pass box according to a first embodiment.
Figure 2:
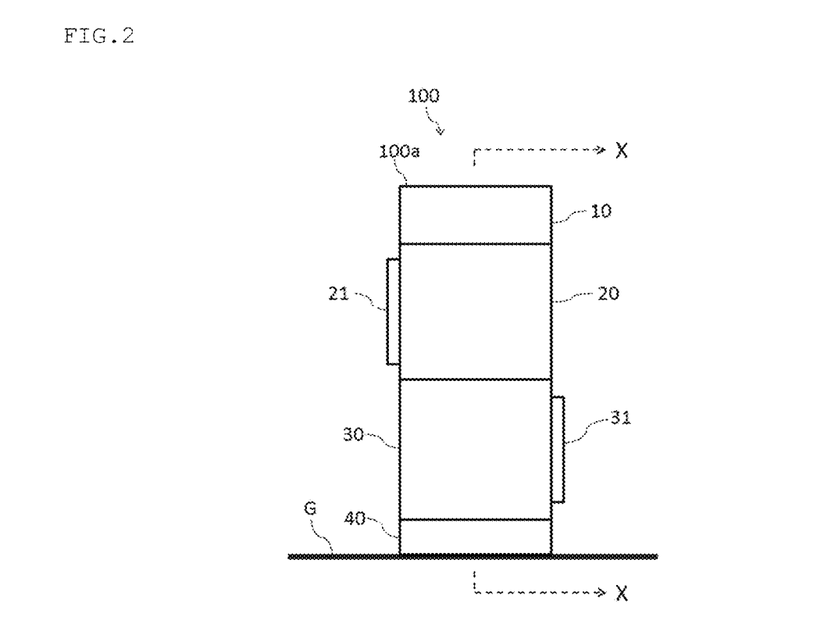
FIG. 2 is a left side view of the pass box of FIG. 1.

FIG. 1 is a front view of a pass box according to a first embodiment, and FIG. 2 is a left side view thereof. In FIGS. 1 and 2, a pass box 100 according to this first embodiment is configured by a pass box body 100a placed on a floor G and an electrical/machine room 100b joined to a wall portion of its right surface. In this first embodiment, a rear surface wall of the pass box 100 is linked to an isolator (not shown) maintained in grade A environment according to medical GMP standards.

The pass box body 100a is, in the order from an upper portion thereof, configured by an upper machine room 10, a second chamber 20 (also referred to as "aeration chamber 20"), a first chamber 30 (also referred to as "decontamination chamber 30") and a lower machine room 40. The upper machine room 10 has therein a supply pipe (later-described) for supplying clean air to the aeration chamber 20. The aeration chamber 20 is composed of a housing made of stainless metal plate, and a rear surface wall thereof is linked to a wall surface of an isolator (not shown) through an opening/closing door 21 (also referred to as "internal door 21") (see FIG. 2). The configuration of the inside of the aeration chamber 20 will be described later.

The decontamination chamber 30 is composed of a housing made of stainless metal plate, and includes an opening/closing door 31 (also referred to as "external door 31") on a front wall thereof leading to the external environment and an opening/closing door (also referred to as "central door"; later-described) leading to the inside of the aeration chamber 20 (see FIG. 1). The details of the inside of the decontamination chamber 30 will be described later. The lower machine room 40 includes therein a decontamination agent supply device (later-described) for supplying a decontamination agent to the decontamination chamber 30 and an exhaust pipe (later-described) for discharging the air in the aeration chamber 20 and the decontamination chamber 30.

The electrical/machine room 100b includes therein an air supply and exhaust device (not shown) for communicating with a supply pipe of the upper machine room 10 and an exhaust pipe of the lower machine room 40, and a control device (not shown) and the like for controlling the pass box body 100a such as a decontamination agent supply device or the like. The electrical/machine room 100b also serves as a control board, and a front wall thereof is provided with a control monitor S1 and a control panel S2 (see FIG. 1).

The linking state between the pass box body 100a and the isolator and the structure of each opening/closing door (internal door 21, external door 31) are not particularly restricted, and the pass box is the same as conventional pass boxes in structure. The wall surface of the pass box linked to the isolator is not restricted to that on a rear surface wall, and the pass box may be linked to a right or left side wall or the like. The inside of the pass box may additionally be provided with an air supply and exhaust device for decontamination and aeration.

Subsequently, using the pass box according to this first embodiment, operations for decontaminating external surfaces of a package P that accommodates a plurality of sterilized containers and conveying the package to the inside of an isolator maintained in grade A environment will be described.

Figure 3:
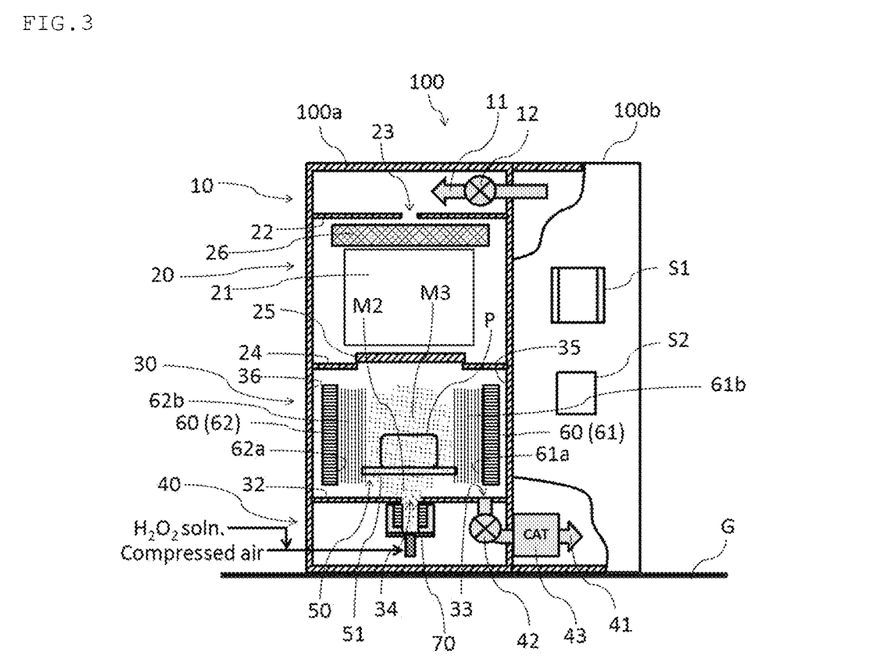
FIG. 3 is a schematic front cross-sectional view showing the inside of (internal contents of) the pass box of FIG. 1 during decontamination.

FIG. 3 is a schematic front cross-sectional view showing the inside of the pass box according to this first embodiment during decontamination, and a cross-sectional view taken from line X-X of FIG. 2 (a partial cross-sectional view for the electrical/machine room 100b). In FIG. 3, the upper machine room 10 is provided with a supply pipe 11 and an on-off valve 12 (each shown in a schematic diagram), each supplying clean air supplied from an air supply mechanism of an air supply and exhaust device (not shown) installed inside the electrical/machine room 100b from a supply port 23 of an air supply and exhaust device that is open at the upper wall 22 of the aeration chamber 20 to the inside of the aeration chamber 20. During the decontamination as shown in FIG. 3, the on-off valve 12 is controlled to be closed by a control device (not shown) of the pass box body 100a to supply no clean air.

The aeration chamber 20 is provided with the supply port 23 of the air supply and exhaust device (not shown) that is open at the above-described upper wall 22, the internal door 21 mounted at an opening communicating the aeration chamber 20 and an isolator (not shown), the central door 25 provided at a communicating portion that is open at the boundary wall 24 between the aeration chamber 20 and the decontamination chamber 30, and a filter fan unit 26 (FFU 26) placed underneath the upper wall 22 of the aeration chamber 20. Prior to the decontamination as shown in FIG. 3, the aeration chamber 20 is decontaminated beforehand and maintained in grade A or grade B environment.

The central door 25 is controlled to be opened and closed by a control device (not shown) of the pass box body 100a. Also, the FFU 26 is disposed such that clean air supplied from the supply port 23 of the air supply and exhaust device (not shown) during aeration is fed as a unidirectional flow from an upper portion of the aeration chamber 20 to a lower portion of the decontamination chamber 30. During the decontamination as shown in FIG. 3, the internal door 21 and the central door 25 are air-tightly closed, and the FFU 26 is controlled to stop by a control device (not shown) of the pass box body 100a.

The decontamination chamber 30 is provided with an exhaust port 33 of an air supply and exhaust device (not shown) that is open at a lower wall 32, a supply port 34 of a decontamination agent supply device 70 (later-described), a moving device 50 for moving a package P from the decontamination chamber 30 to the aeration chamber 20, and a decontamination agent control device 60 (later-described in detail). In this first embodiment, the moving device 50 used is a lifting device 50. The lifting device 50 is configured by a table 51 on which a package P is placed and an elevating/lowering unit (not shown) for allowing the table 51 to elevate and lower between the decontamination chamber 30 and the aeration chamber 20, which is controlled to elevate and lower by a control device (not shown) of the pass box body 100a. The shape of the table is not particularly restricted, and may be a mesh structure or the like for efficiently decontaminating a bottom surface portion of the package P. In addition, as a structure of providing the surface of a table with irregularities, the bottom surface portion of the package P may efficiently be decontaminated by ultrasonic vibration. Moreover, the package P may be provided in a suspended fashion without using a table. Meanwhile, the system and structure of an elevating/lowering unit may be any type such as manual hoisting, lift system or robot arm.

The lower machine room 40 is provided with a decontamination agent supply device 70 for supplying a decontamination agent to the decontamination chamber 30, which supplies the decontamination agent to the inside of the decontamination chamber 30 from the supply port 34 that is open at the lower wall 32 of the decontamination chamber 30. During the decontamination as shown in FIG. 3, the decontamination agent is controlled to be supplied by a control device (not shown) of the pass box body 100a. In addition, the lower machine room 40 is provided with an exhaust pipe 41, an on-off valve 42, and a catalyst unit 43 for resolving the decontamination agent (each shown in a schematic diagram), and the air flowing out of the aeration chamber 20 and the decontamination chamber 30 is sucked out by suction from the exhaust mechanism of an air supply and exhaust device (not shown) installed inside the electrical/machine room 100b to resolve the decontamination agent contained in the air and discharge the same into the external environment. During the decontamination as shown in FIG. 3, the on-off valve 42 is controlled to be closed by a control device (not shown) of the pass box body 100a to discharge no air.

Subsequently, a decontamination operation as a first feature of the present invention will be described. The decontamination operation is performed in the decontamination chamber 30. In FIG. 3, the package P is conveyed from the external environment onto the table 51 of the moving device 50 at a center lower portion inside the decontamination chamber 30. In this first embodiment, external surfaces of the package P are to be decontaminated. In FIG. 3, inside the decontamination chamber 30, the decontamination agent is supplied through the supply port 34 from the decontamination agent supply device 70 of the lower machine room 40.

Figure 5:
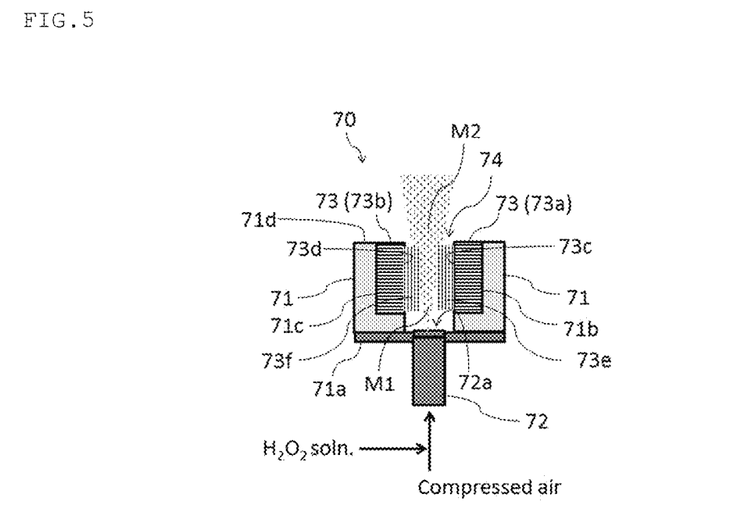
FIG. 5 is a schematic front cross-sectional view showing a decontamination agent supply device included in the pass box of FIG. 1.

Herein, the decontamination agent supply device 70 according to this first embodiment will be described. FIG. 5 is a schematic front cross-sectional view showing a decontamination agent supply device included in the pass box in FIG. 1 according to this first embodiment. In FIG. 5, the decontamination agent supply device 70 includes a housing 71 made of stainless metal plate, a mist generation unit 72 for generating a primary mist, a mist microparticulating unit 73 for further miniaturizing (reducing in size) the generated primary mist into a secondary mist, and a supply port 74 for discharging the generated secondary mist.

The mist generation unit 72 converts a decontamination agent into a primary mist and supplies the same to the mist microparticulating unit 73. In this first embodiment, the mist generation unit 72 used is a two-fluid spray nozzle 72, which is disposed on a bottom wall surface 71a of the housing 71. In this first embodiment, the decontamination agent used is a hydrogen peroxide solution (35 W/V %).

The two-fluid spray nozzle 72 converts a hydrogen peroxide solution into a hydrogen peroxide solution mist M1 as a primary mist by compressed air from a compressor (not shown) to supply the same to the mist microparticulating unit 73. In the first embodiment, the mist generation unit used is a two-fluid spray nozzle, but it is not restricted thereto, and a mist generation unit and output are not particularly restricted.

In this first embodiment, 2 vibration boards 73a, 73b are used as the mist microparticulating unit 73 and disposed against the inside of 2 side wall surfaces 71b, 71c opposite the housing 71 such that vibration surfaces 73c, 73d face in the horizontal direction toward an upper portion of the mist discharge port 72a of the two-fluid spray nozzle 72. The mist microparticulating unit 73 miniaturizes the hydrogen peroxide solution mist M1 generated as the primary mist by the two-fluid spray nozzle 72 into a fine mist M2 as a secondary mist. The details of miniaturizing will be described later.

The supply port 74 is open on an upper wall surface 71d of the housing 71, and connected to the supply port 34 that is open at the lower wall 32 of the decontamination chamber 30. Through the supply port 74 (the supply port 34 of the decontamination chamber 30), the mist microparticulating unit 73 supplies the fine mist M2 miniaturized as a secondary mist to the inside of the decontamination chamber 30. The details of the vibration board 73 will be described later. In this first embodiment, a mist microparticulating unit is employed, but the unit is not restricted thereto in this invention, and the primary mist generated from the mist generation unit may be directly supplied to the inside of the decontamination chamber 30 without employing a mist microparticulating unit.

Figure 4:
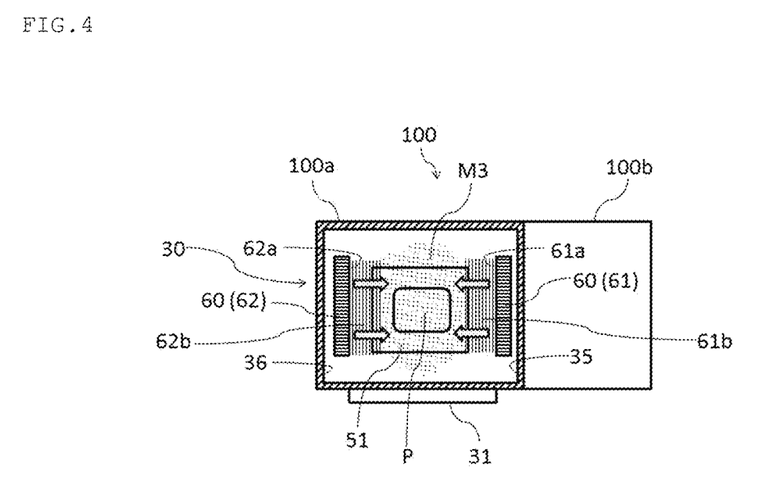
FIG. 4 is a schematic plan cross-sectional view showing the inside of a first chamber of the pass box of FIG. 1 during decontamination.

Herein, a decontamination agent control device 60 will be described. FIG. 4 is a schematic plan cross-sectional view showing the inside of a first chamber (decontamination chamber) during decontamination, and a cross-sectional view taken from line Y-Y of FIG. 1. In the front cross-sectional view in FIG. 3 and the plan cross-sectional view in FIG. 4 regarding the decontamination chamber 30, the decontamination agent control device 60 includes 2 vibration boards 61, 62. The vibration boards 61, 62 are disposed inside the decontamination chamber 30 against left and right side walls 35, 36 such that vibration surfaces 61a, 62a face horizontally inside the decontamination chamber 30. These 2 vibration boards 61, 62 are arranged by allowing board surfaces (vibration surfaces) thereof to be opposite each other (the board surfaces to face each other in front) (see FIG. 4). The reason for arranging these vibration boards by allowing them to be opposite each other and the action of the fine mist M2 supplied to the inside of the decontamination chamber 30 will be described later.

Figure 6:
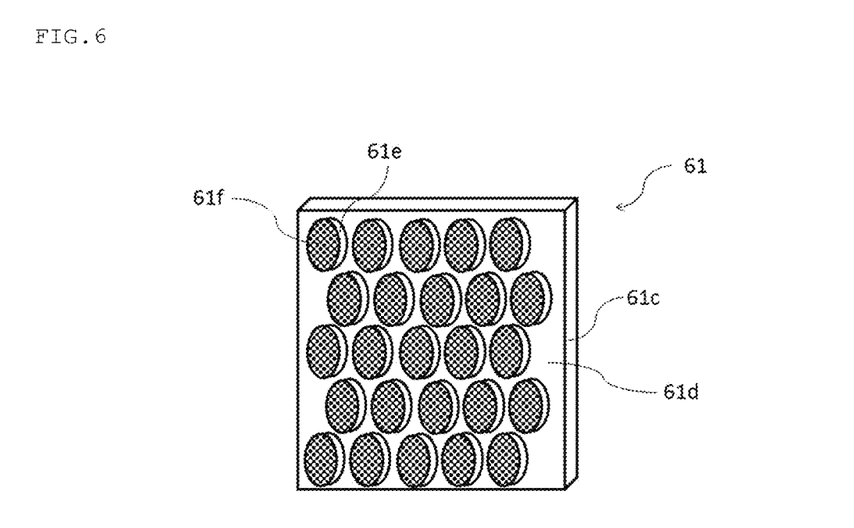
FIG. 6 is a schematic perspective view showing a plurality of ultrasonic speakers arranged in a speaker base in a vibration board included in the pass box of FIG. 1.

Herein, the vibration boards will be described. In this first embodiment, 2 vibration boards 61, 62, of the decontamination agent control device 60 and 2 vibration boards 73a, 73b of the mist microparticulating unit 73 are used. These vibration boards basically have the same structures and functions. Herein, the vibration board 61 of the decontamination agent control device 60 will be illustrated. FIG. 6 is a schematic perspective view showing a plurality of ultrasonic speakers arranged in a speaker base in a vibration board included in the pass box according to this first embodiment. In FIG. 6, the vibration board 61 includes a base and a plurality of transmitters. In this first embodiment, the base used is a speaker base 61c, and the transmitter used is an ultrasonic speaker 61e. In this first embodiment, 25 ultrasonic speakers 61e are arranged on a plain surface 61d of the speaker base 61c so as to be uniform in transmission direction of a vibration surface 61f thereof (leftward as seen from the front shown). The number of ultrasonic speakers is not particularly restricted.

In this first embodiment, the ultrasonic speaker 61e used is an ultra-directional ultrasonic speaker. Specifically, ultrasonic speakers (DC 12V, 50 mA) of frequency modulation system transmitting a frequency near 40 KHz are used. The type, size, structure and output of the ultrasonic speaker are not particularly restricted. In the present invention, the vibration board included in the decontamination agent control device 60 or the mist microparticulating unit 73 is not restricted to an ultrasonic speaker, and the ultrasonic generation mechanism, frequency range and output are not particularly restricted.

In this first embodiment, a plurality of (25) ultrasonic speakers 61e are arranged so as to be uniform in transmission direction of the vibration surface 61f, and the transmitters are operated in the same phase to mutually amplify ultrasounds from the plurality of ultrasonic speakers 61e in the front direction and mutually cancel out ultrasounds from the plurality of ultrasonic speakers 61e in the lateral direction. Consequently, the ultrasonic speakers 61e arranged on the speaker base 61c ultrasonically vibrate to generate a significantly directional sound flow traveling in the air from each of the vibration surfaces 61f in the vertical direction. The frequency and output of each of the ultrasonic speakers 61e of the decontamination agent control device 60 and the mist microparticulating unit 73 are controlled by a control device (not shown) of the pass box body 100a to achieve efficient decontamination operations inside the decontamination chamber 30.

Subsequently, the action of the hydrogen peroxide solution mist in the decontamination agent supply device 70 and the decontamination agent control device 60 according to this first embodiment will be described. First, the action of the hydrogen peroxide solution mist in the decontamination agent supply device 70 will be described.

In FIG. 5, the hydrogen peroxide solution mist M1 generated as the primary mist by the two-fluid spray nozzle 72 is supplied to the mist microparticulating unit 73. Ultrasonic vibration of the ultrasonic speaker 61e of the 2 vibration boards 73a, 73b of the mist microparticulating unit 73 in this state generates significantly directional sound flows 73e, 73f traveling in the vertical direction from 2 vibration surfaces 73c, 73d, respectively. The sound flows 73e, 73f generated from the vibration surfaces 73c, 73d of the vibration boards 73a, 73b act on the hydrogen peroxide solution mist M1 discharged from the two-fluid spray nozzle 72. The hydrogen peroxide solution mist M1 travels upward in the figure shown (in the direction of the supply port 74) by a releasing pressure from the two-fluid spray nozzle 72.

At this time, the hydrogen peroxide solution mist M1 as a primary mist is miniaturized into a secondary mist M2 by ultrasonic vibration by the sound flows generated from the vibration surfaces 73c, 73d, and travels upward in the figure shown to be supplied to the inside of the decontamination chamber 30 communicating with an upper portion from the supply port 74 (connected to the supply port 34 that is open at the lower wall 32 of the decontamination chamber 30). In fact, since the fine mist M2 is miniaturized by ultrasonic vibration to have smaller particle sizes and larger surface areas, it is believed that the evaporation efficiency of mists is high, resulting in repeated evaporation and condensation to be supplied to the inside of the decontamination chamber 30 as a highly miniaturized mist.

Subsequently, the action of the fine mist M2 supplied inside the decontamination chamber 30 will be described. In FIGS. 3 and 4, the vibration boards, 61, 62 placed at 2 side walls 35, 36 inside the decontamination chamber 30 allow vibration surfaces 61a, 62a thereof to face the central portion of the decontamination chamber 30 (in the same direction as the direction of the vibration surface 61f of the ultrasonic speaker 61e).

Ultrasonic vibration of the ultrasonic speaker 61e of each vibration board in this state generates significantly directional sound flows 61b, 62b traveling in the vertical direction from the 2 vibration surfaces 61a, 62a, respectively. These sound flows 61b, 62b take in the fine mist M2 discharged from the mist microparticulating unit 73 through the supply port 34 to move the mist to the central portion of the decontamination chamber 30 each by pressing force from acoustic radiation pressure. In this case, the hydrogen peroxide solution mist M2 is further miniaturized into an ultrafine mist M3 by the ultrasonic vibration from the sound flows 61b, 62b.

In FIG. 4, the 2 vibration boards 61, 62 are arranged with the package P interposed therebetween such that their vibration surfaces 61a, 62a are opposite. In this state, the package P conveyed to the central portion of the decontamination chamber 30 is interposed between the respective vibration surfaces 61a, 62a of the 2 vibration boards 61, 62. Inventors of the present invention found that in this state the ultrafine mist M3 further miniaturized by ultrasonic vibration from the sound flows 61b, 62b concentrates from both sides on external surfaces of the package P located at the central portion of the decontamination chamber 30 (see FIGS. 3 and 4). The reason has not clearly been identified, but this is probably because acoustic waves generated from each vibration board reach the article but only partially reflect off the same to primarily absorb or scatter on the surface of the article, thereby allowing the pressing force of the acoustic radiation pressure to concentrate in the article's direction.

In fact, since the ultrafine mist M3 is ultra-miniaturized by ultrasonic vibration to have extremely smaller particle sizes and larger surface areas, it is believed that the evaporation efficiency of mists is high, resulting in repeated evaporation and condensation. The ultrafine mist M3 is a highly-miniaturized mist to concentrate on the external surfaces of the package P and form a uniform and thin condensed film on the external surfaces of the package P. Therefore, no excessive condensation occurs on internal wall surfaces of the decontamination chamber 30.

Thus, the ultrafine mist M3 of hydrogen peroxide is subjected to constant ultrasonic vibration to concentrate on the periphery of the package P with repeated evaporation, condensation, and miniaturizing. Even on the external surfaces of the package P, the fine mist is subjected to constant ultrasonic vibration to cause repeated re-evaporation and condensation of a uniform and thin condensed film. Accordingly, it is believed that ultrafine particles of hydrogen peroxide 3 µm or less and a hydrogen peroxide gas are subjected to phase change for coexistence on the periphery of the package P to provide high-level decontamination environment.

Also, by repeated re-evaporation and condensation of the uniformly and thinly formed condensed film on the external surfaces of the package P, the concentration of a decontamination agent in a hydrogen peroxide solution mist can be increased and efficient decontamination can be performed with a small amount of decontamination agent. Such an efficient decontamination with a small amount of decontamination agent can significantly reduce the decontamination time. Inventors of the present invention confirmed that the time required for decontaminating a package P, for specimens or the like, is approx. 3 to 5 minutes if sized about 10 to 100 mm, and approx. 10 to 20 minutes if sized about 300×300 mm. Furthermore, the secondary effect is that ultrasonic vibration and acoustic radiation pressure by the sound flows 61b, 62b can remove a deposit on external surfaces of the package P.

Subsequently, an aeration operation as a second feature of the present invention will be described. The aeration operation is performed in the aeration chamber 20. First, after the package P is completely decontaminated in the decontamination chamber 30, the decontamination agent supply device 70 and the decontamination agent control device 60 are controlled to stop by a control device (not shown) of the pass box body 100a. Subsequently, an air supply mechanism and an exhaust mechanism of an air supply and exhaust device (not shown) installed inside the electrical/machine room 100b is operated by a control device. At this time, the central door 25 is controlled to be opened by the control device to communicate the aeration chamber 20 and the decontamination chamber 30.

Figure 7:
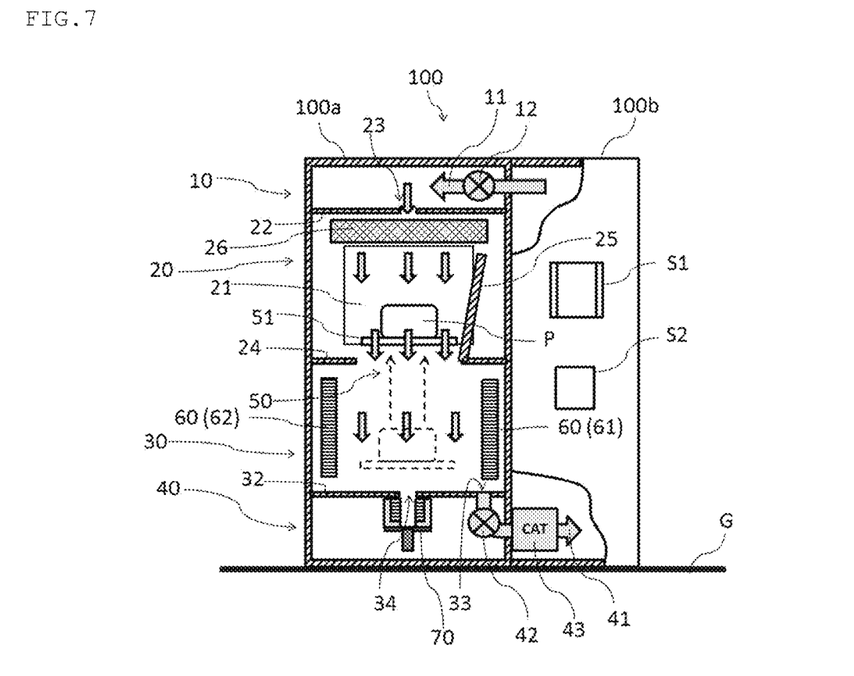
FIG. 7 is a schematic front cross-sectional view showing the inside of (internal contents of) the pass box of FIG. 1 during aeration.

FIG. 7 is a schematic front cross-sectional view showing the inside during aeration according to this first embodiment. In FIG. 7, the on-off valve 12 of the upper machine room 10 is opened to allow clean air from the air supply mechanism to be supplied to the inside of the aeration chamber 20 through the supply pipe 11 and the supply port 23. In response thereto, the FFU 26 disposed underneath the supply port 23 is also operated. Also, the on-off valve 42 of the lower machine room 40 is opened to allow the air in the aeration chamber 20 and the decontamination chamber 30 to be discharged by suction from the exhaust mechanism to the external environment through the exhaust port 33 and the exhaust pipe 41. At this time, the hydrogen peroxide contained in the discharged air is resolved by the catalyst unit 43.

In FIG. 7, the package P is moved to the aeration chamber 20 by an elevating/lowering unit (not shown) (the original position shown by a broken line in FIG. 7) while it is placed on the table 51 of the lifting device 50. In this state, the clean air supplied through the supply port 23 of the aeration chamber 20 is converted into a unidirectional flow (as shown by arrows in FIG. 7) from an upper portion of the aeration chamber 20 to a lower portion of the decontamination chamber 30 by a fan of the FFU 26 and discharged into the external environment through the exhaust port 33 of the decontamination chamber 30 while the external surfaces of the package P and the inside of the decontamination chamber 30 are aerated. Accordingly, in this first embodiment, since aeration is performed by a unidirectional flow from the upper side to the lower side, the aeration chamber 20 is preferably disposed at an upper portion of the decontamination chamber 30.

As stated above, in the decontamination operation according to this first embodiment, the ultrafine mist M3 is a highly-miniaturized mist to concentrate on the external surfaces of the package P and form a uniform and thin condensed film on the external surfaces of the package P. Therefore, in the aeration operation in this first embodiment, the aeration chamber 20 is separated from the decontamination chamber 30, and a condensed film to be removed is thin, resulting in improved aeration efficiency and reduced duration of decontamination. Inventors of the present invention confirmed that the effective time required for aerating a package P is approx. 1 to 2 minutes. Once the package P has been aerated, it is conveyed through the internal door 21 to the inside of an isolator with grade A maintained.

Thus, according to this first embodiment, the present invention can provide a pass box capable of accomplishing a decontamination effect with a proper amount of decontamination agent by concentrating a mist for decontamination on the surface of an article to be conveyed to grade A environment, and of achieving more efficient decontamination works by reducing the duration of aeration operations.

Second Embodiment

Figure 8:
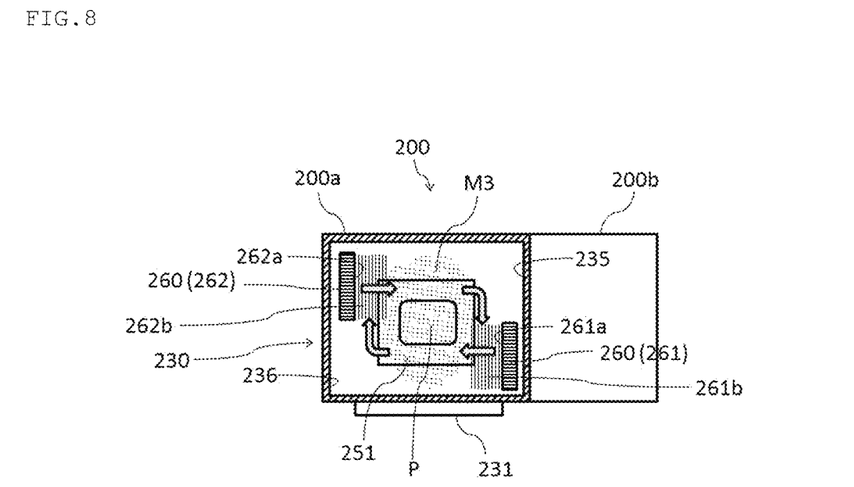
FIG. 8 is a schematic plan cross-sectional view showing the inside of a first chamber of a pass box according to a second embodiment during decontamination.

While the decontamination agent control device according to the above first embodiment relates to a pass box including in a decontamination chamber 2 vibration boards that are opposite each other, this second embodiment relates to a pass box including in a decontamination chamber 2 vibration boards that are not opposite each other. FIG. 8 is a schematic plan cross-sectional view showing the inside of a first chamber (decontamination chamber) of the pass box according to a second embodiment during decontamination. A schematic front cross-sectional view showing the inside of the pass box according to this second embodiment during decontamination and a schematic front cross-sectional view showing the inside of the pass box during aeration are the same as in the above first embodiment (see FIGS. 3 and 7).

In FIG. 8, a pass box 200 according to this second embodiment is configured by a pass box body 200a and an electrical/machine room 200b joined to a wall portion of its right surface. The pass box body 200a is, as in the above first embodiment, in the order from an upper portion thereof, configured by an upper machine room, a second chamber (also referred to as "aeration chamber"), a first chamber 230 (also referred to as "decontamination chamber 230") and a lower machine room (the inside of the decontamination chamber 230 only shown in FIG. 8). The configurations of the upper machine room, the aeration chamber, the lower machine room and the electrical/machine room 200b are the same as in the above first embodiment (see FIGS. 3 and 7).

The decontamination chamber 230 is composed of a housing made of stainless metal plate, and includes an opening/closing door 231 (also referred to as "external door 231") on a front wall thereof leading to the external environment and an opening/closing door (not shown) leading to the inside of the aeration chamber 220. In the plan cross-sectional view in FIG. 8, the decontamination agent control device 260 includes 2 vibration boards 261, 262. The vibration boards 261, 262 are the same as the vibration boards 61, 62 in the above first embodiment in structure (see FIG. 6). The frequency and output of these vibration boards 261, 262 are also the same as those of the vibration boards in the above first embodiment.

Subsequently, the action of a fine mist M2 supplied to the inside of the decontamination chamber 230 will be described. Also in this second embodiment, the hydrogen peroxide solution mist is the fine mist M2 supplied from the decontamination agent supply device as in the above first embodiment. In FIG. 8, the 2 vibration boards 261, 262 are disposed inside the decontamination chamber 230 against side wall surfaces at 2 portions: a lower portion of a right wall surface 235 and an upper portion of a left wall surface 236 shown such that vibration surfaces 261a, 262a face horizontally inside the decontamination chamber 230. These 2 vibration boards 261, 262 are arranged without allowing board surfaces (vibration surfaces) thereof to be opposite each other.

The vibration table 261 placed at the right lower portion shown inside the decontamination chamber 230 allows the vibration surface 261a thereof to face in the left direction shown. Ultrasonic vibration of the ultrasonic speaker 61e of each vibration board in this state allows a significantly directional sound flow 261b traveling in the vertical direction (in the left direction shown) from the vibration surface 261a to take in a fine mist M2 discharged from the mist microparticulating unit through a supply port (not shown) to move the same in the direction of the sound flow 261b (in the left direction shown) by pressing force from acoustic radiation pressure. In this case, the hydrogen peroxide solution mist M2 is converted into an ultrafine mist M3 that is further miniaturized by ultrasonic vibration from the sound flow 261b and circulates so as to rotate inside the decontamination chamber 230.

Meanwhile, the vibration table 262 placed at the left upper portion shown inside the decontamination chamber 230 allows the vibration surface 262a thereof to face in the right direction shown. Ultrasonic vibration of the ultrasonic speaker 61e in this state allows a significantly directional sound flow 262b traveling in the vertical direction (in the right direction shown) from the vibration surface 262a to move the same in the direction of the sound flow 262b (in the right direction shown) by pressing force from acoustic radiation pressure on the ultrafine mist M3 miniaturized and sent by the sound flow 261b. In this case, the hydrogen peroxide solution mist M3 is converted into an ultrafine mist that is further stabilized by ultrasonic vibration from the sound flow 262b and circulates so as to rotate inside the decontamination chamber 230.

Thus, inside the decontamination chamber 230, the ultrafine mist M3 miniaturized and stabilized by the sound flows 261b and 262b circulate so as to rotate the mist in the curved arrow direction shown in FIG. 8 (clockwise). Inventors of the present invention found that the ultrafine mist M3 miniaturized by ultrasonic vibration from the sound flows 261b 262b in this state circulates so as to rotate the mist by concentrating it around the external surfaces of the package P located at the central portion of the decontamination chamber 230 (see FIG. 8). The reason has not clearly been identified, but this is probably because acoustic waves generated from each vibration board reach the article to diffract primarily along a side surface of the package P from each vibration board.

In fact, since the ultrafine mist M3 is ultra-miniaturized by ultrasonic vibration to have extremely smaller particle sizes and larger surface areas, it is believed that the evaporation efficiency of mists is high, resulting in repeated evaporation and condensation. The ultrafine mist M3 is a highly-miniaturized mist to concentrate on the external surfaces of the package P and form a uniform and thin condensed film on the external surfaces of the package P. Therefore, no excessive condensation occurs on internal wall surfaces of the decontamination chamber 230.

Thus, the ultrafine mist M3 of hydrogen peroxide is subjected to constant ultrasonic vibration to concentrate on the periphery of the package P with repeated evaporation, condensation, and miniaturizing. Even on the external surfaces of the package P, the fine mist is subjected to constant ultrasonic vibration to cause repeated re-evaporation and condensation of a uniform and thin condensed film. Accordingly, it is believed that ultrafine particles of hydrogen peroxide 3 μm or less and a hydrogen peroxide gas are subjected to phase change for coexistence on the periphery of the package P to provide high-level decontamination environment.

Also, by repeated re-evaporation and condensation of the uniformly and thinly formed condensed film on the external surfaces of the package P, the concentration of a decontamination agent in a hydrogen peroxide solution mist can be increased and efficient decontamination can be performed with a small amount of decontamination agent. Such an efficient decontamination with a small amount of decontamination agent can significantly reduce the decontamination time. Inventors of the present invention confirmed that the time required for decontaminating a package P, for specimens or the like, is approx. 3 to 5 minutes if sized about 10 to 100 mm, and approx. 10 to 20 minutes if sized about 300×300 mm. Furthermore, the secondary effect is that ultrasonic vibration and acoustic radiation pressure by the sound flows 261b, 262b can remove a deposit on external surfaces of the package P. An aeration operation in this second embodiment can be performed as in the above first embodiment.

As stated above, in the decontamination operation according to this second embodiment, the ultrafine mist M3 is a highly-miniaturized mist to concentrate on the external surfaces of the package P and form a uniform and thin condensed film on the external surfaces of the package P. Therefore, in the aeration operation according to this first embodiment, the aeration chamber is separated from the decontamination chamber, and a condensed film to be removed is thin, resulting in improved aeration efficiency and reduced duration of decontamination. Inventors of the present invention confirmed that the effective time required for aerating a package P is approx. 1 to 5 minutes.

Thus, according to this second embodiment, the present invention can provide a pass box capable of accomplishing a decontamination effect with a proper amount of decontamination agent by concentrating a mist for decontamination on the surface of an article to be conveyed to grade A environment, and of achieving more efficient decontamination works by reducing the duration of aeration operations.

Third Embodiment

Figure 9:
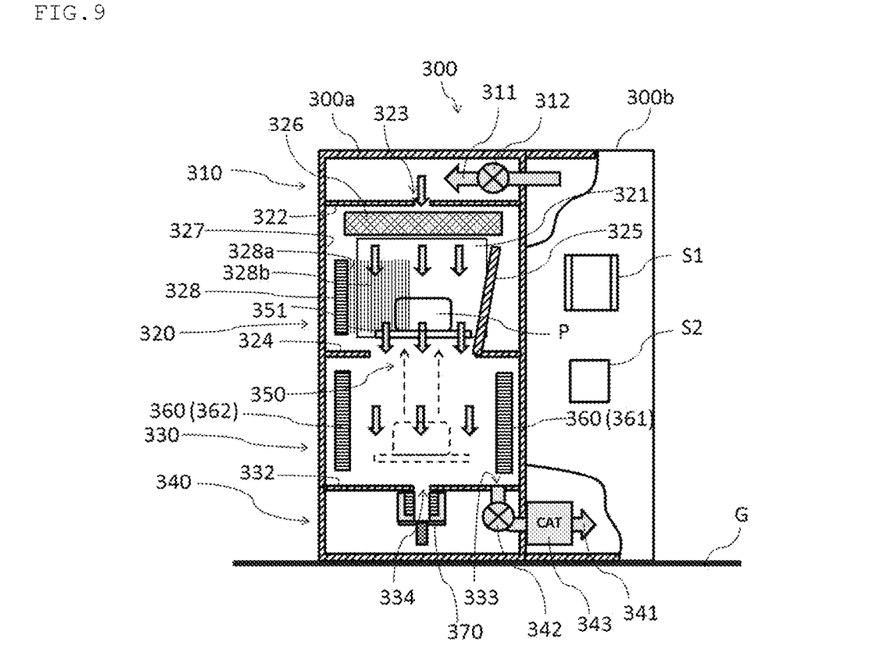
FIG. 9 is a schematic front cross-sectional view showing the inside of a pass box according to a third embodiment during aeration.

In the above first embodiment, no vibration board is used during aeration, but in this third embodiment, the case where a vibration board is used even during aeration will be described. FIG. 9 is a schematic front cross-sectional view showing the inside of a pass box according to this third embodiment during aeration. An operation for decontaminating the pass box according the third embodiment can be performed as in the above first and second embodiments except the way a vibration board provided in an aeration chamber is operated.

In FIG. 9, a pass box 300 according to this third embodiment is configured by a pass box body 300a and an electrical/machine room 300b joined to a wall portion of its right surface. The pass box body 300a is, as in the above first embodiment, in the order from an upper portion thereof, configured by an upper machine room 310, a second chamber 320 (also referred to as "aeration chamber 320"), a first chamber 330 (also referred to as "decontamination chamber 330"), and a lower machine room 340. The configurations of the upper machine room 310, the decontamination chamber 330, the lower machine room 340 and the electrical/machine room 300b are the same as in the above first embodiment (see FIGS. 3, 4, 5 and 7).

In FIG. 9, the upper machine room 310 is, as in the above first embodiment, provided with a supply pipe 311 and an on-off valve 312 (each shown in a schematic diagram), each supplying the clean air supplied from an air supply mechanism of an air supply and exhaust device (not shown) installed inside the electrical/machine room 300b from the supply port 323 of an air supply and exhaust device that is open at the upper wall 322 of the aeration chamber 320 to the inside of the aeration chamber 320. During the aeration as shown in FIG. 9, the on-off valve 312 is controlled to be open by a control device (not shown) of the pass box body 300a to supply clean air.

The aeration chamber 320 is provided with the supply port 323 of the air supply and exhaust device (not shown) that is open at the above-described upper wall 322, the internal door 321 mounted at an opening communicating the aeration chamber 320 and an isolator (not shown), a central door 325 provided at a communicating portion that is open at the boundary wall 324 between the aeration chamber 320 and the decontamination chamber 330, and a filter fan unit 326 (FFU 326) placed underneath the upper wall 322 of the aeration chamber 320. In this third embodiment, one vibration board 328 is disposed inside the aeration chamber 320 against a left side wall 327 such that a vibration surface 328a faces horizontally inside the aeration chamber 320.

The aeration operation in this third embodiment is performed in the aeration chamber 320. First, after a package P is completely decontaminated in the decontamination chamber 330, a decontamination agent supply device 370 and a decontamination agent control device 360 are controlled to stop by a control device (not shown) of the pass box body 300a. Subsequently, an air supply mechanism and an exhaust mechanism of an air supply and exhaust device (not shown) installed inside the electrical/machine room 300b are operated by a control device. At this time, the central door 325 is opened by the control device to communicate the aeration chamber 320 and the decontamination chamber 330.

In FIG. 9, the on-off valve 312 of the upper machine room 310 is opened to allow the clean air from the air supply mechanism to be supplied to the inside of the aeration chamber 320 through the supply pipe 311 and the supply port 323. In response thereto, the FFU 326 disposed underneath the supply port 323 is also operated. In addition, the on-off valve 342 of the lower machine room 340 is opened to allow the air in the aeration chamber 320 and the decontamination chamber 330 to be discharged by suction from the exhaust mechanism to the external environment through the exhaust port 333 and the exhaust pipe 341. At this time, the hydrogen peroxide contained in the discharged air is resolved by the catalyst unit 343. In this third embodiment, the vibration board 328 is operated during aeration.

In FIG. 9, the package P is moved to the aeration chamber 320 by an elevating/lowering unit (not shown) (the original position shown by a broken line in FIG. 9) while it is placed on the table 351 of the lifting device 350. In this state, the clean air supplied through the supply port 323 of the aeration chamber 320 is converted into a unidirectional flow (as shown by arrows in FIG. 9) from an upper portion of the aeration chamber 320 to a lower portion of the decontamination chamber 330 by a fan of the FFU 326 and discharged into the external environment through the exhaust port 333 of the decontamination chamber 330 while the external surfaces of the package P and the inside of the decontamination chamber 330 are aerated. Accordingly, in this third embodiment, since aeration is performed by a unidirectional flow from the upper side to the lower side, the aeration chamber 320 is preferably disposed at an upper portion of the decontamination chamber 330.

In an aeration operation according to this third embodiment, an ultrafine mist M3 forms a uniform and thin condensed film on the external surfaces of the package P. The supply of the unidirectional flow of clean air by the action of the FFU 326 fan in this state and ultrasonic vibration of the ultrasonic board 328 generate significantly directional sound flows 328b traveling in the vertical direction from the vibration surface 328a. The sound flow 328b allows pressing forces by ultrasonic vibration and acoustic radiation pressure to act on the external surfaces of the package P. Accordingly, a thin condensed film formed on the external surfaces of the package P is vibrated, and the condensed film is proactively dried by the action of clean air, resulting in higher aeration effects. Once the package P has been aerated, it is conveyed through the internal door 321 to the inside of an isolator with grade A maintained.

Therefore, in the aeration operation according to this third embodiment, the aeration chamber 320 is separated from the decontamination chamber 330, and the action of the vibration board further improves the aeration efficiency and reduce the duration of aeration.

Thus, according to this third embodiment, the present invention can provide a pass box capable of accomplishing a decontamination effect with a proper amount of decontamination agent by concentrating a mist for decontamination on the surface of an article to be conveyed to grade A environment, and of achieving more efficient decontamination works by reducing the duration of aeration operations.

The present invention is achieved by not only each of the above embodiments, but also by the following various alternatives.

(1) In each of the above embodiments, a decontamination agent supply device used is a combination of a mist generation unit and a mist microparticulating unit. However, the decontamination agent supply device is not restricted thereto, and a decontamination agent mist may directly be supplied from a mist generation unit to a decontamination chamber.

(2) In each of the above embodiments, a mist generation unit of a decontamination agent supply device used is a two-fluid spray nozzle. However, the mist generation unit is not restricted thereto, and it may be other spray nozzle such as a single-fluid nozzle, or an ultrasonic mist generator such as an ultrasonic humidifier, a nebulizer or a piezo atomizer. Also, a combination of a plurality of mist supply devices may be used.

(3) In each of the above embodiments, vibration boards used in a mist microparticulating unit, a mist control device and an aeration chamber include a plurality of ultrasonic speakers arranged in a speaker base. However, the vibration board is not restricted thereto, and any type of vibration board may be used so long as it includes a Langevin type transducer fixed to a stainless steel having a constant area or a board surface for ultrasonic vibration.

(4) In each of the above embodiments, vibration boards used in a mist microparticulating unit, a mist control device and an aeration chamber include a plurality of ultrasonic speakers arranged in a speaker base so as to be uniform in transmission directions of the ultrasonic speakers, and the ultrasonic speakers are operated in the same phase. However, the vibration boards are not restricted thereto, and a plurality of ultrasonic speakers may be operated in a different phase.

(5) In each of the above embodiments, a decontamination agent used is a hydrogen peroxide solution ($H_2O_2$ solution). However, the decontamination agent is not restricted thereto, and it may be any type of decontamination agent so long as it is liquid.

(6) In each of the above embodiments, 2 vibration boards are arranged on side walls of the decontamination chamber. However, the configuration is not restricted thereto, and vibration boards may be arranged on 1 to 6 vibration boards out of 6 boards including other side walls, a top wall surface and a bottom wall surface.

(7) In the above first embodiment, 2 vibration boards are arranged so as to be opposite each other in the decontamination chamber. However, the positional relationship is not restricted thereto, and ultrasonic reflection boards may be arranged so as to be opposite each other relative to one vibration board.

(8) In the above second embodiment, the circulating direction of a decontamination agent mist is horizontal direction in cases where 2 vibration boards are arranged on 2 side walls so as not to be opposite each other in the decontamination chamber. However, the circulation direction is not restricted thereto, and the circulating direction of a decontamination agent mist may be vertical direction in cases where 2 vibration boards may be arranged on a top wall and a bottom wall so as not to be opposite each other.

(9) In the above second embodiment, the circulating direction of a decontamination agent mist is horizontal direction in cases where 2 vibration boards are arranged on 2 side walls so as not to be opposite each other. However, the circulation direction is not restricted thereto, and the circulating direction of a decontamination agent mist may be horizontal direction in cases where 4 vibration boards may be arranged on 4 side walls so as not to be opposite each other.

(10) In each of the above embodiments, a moving device for moving a package from a decontamination chamber to an aeration chamber employed is a lifting device. However, the moving device is not restricted thereto, and other moving devices such as a lift and a robot arm may be used.

(11) In each of the above embodiments, a decontamination chamber and an aeration chamber are disposed in the vertical direction. However, the arrangement is not restricted thereto, and they may be arranged laterally so long as the flow of the air in the both chambers during aeration can be controlled.

REFERENCE SIGNS LIST 100, 200, 300 . . . Pass box,
100a, 200a, 300a . . . Pass box body,
100b, 200b, 300b . . . Electrical/machine room,
10, 310 . . . Upper machine room,
11, 311 . . . Supply pipe,
12, 312 . . . On-off valve,
20, 320 . . . Second chamber (Aeration chamber),
21, 321 . . . Opening/closing door (Internal door),
22, 322 . . . Upper wall,
23, 323 . . . Supply port,
24, 324 . . . Boundary wall,
25, 325 . . . Opening/closing door (Central door),
26, 326 . . . Filter fan unit (FFU),
327 . . . Side wall,
328 . . . Vibration board,
328a . . . Vibration surface,
328b . . . Sound flow,
30, 230, 330 . . . First chamber (Decontamination chamber),
31, 231 . . . Opening/closing door (External door),
32 . . . Lower wall,
33, 333 . . . Exhaust port,
34, 334 . . . Supply port,
35, 36 . . . Side wall,
40, 340 . . . Lower machine room,
41, 341 . . . Exhaust pipe,
42, 342 . . . On-off valve,
43, 343 . . . Catalyst unit,
50, 350 . . . Moving device,
51, 351 . . . Table,
60 . . . Decontamination agent control device,
61, 62, 261, 262 . . . Vibration board,
61a, 62a, 261a, 262a . . . Vibration surface,
61b, 62b, 261b, 262b . . . Sound flow,
61c . . . Speaker base,
61d . . . plane or planar surface of speaker base,
61e . . . Ultrasonic speaker,
61f . . . Vibration surface,
70, 370 . . . Decontamination agent supply device,
71 . . . Housing,
71a . . . Bottom wall surface,
71b, 71c . . . Side wall surface,
71d . . . Upper wall surface,
72 . . . Mist generation unit (Two-fluid spray nozzle),
72a . . . Discharge port,
73 . . . Mist microparticulating unit,
73a, 73b . . . Vibration board,
73c, 73d . . . Vibration surface,
73e, 73f . . . Sound flow,
74 . . . Supply port,
M1 . . . Hydrogen peroxide solution mist,
M2 . . . Fine mist,
M3 . . . Ultrafine mist,
S1 . . . Control monitor,
S2 . . . Control panel,
G . . . Floor.

The invention claimed is:

1. A pass box configured to convey an article therethrough and deliver said article to a location outside the pass box, the pass box comprising:
a first chamber dimensioned to receive the article therein and configured to decontaminate external surfaces of the article with a decontamination agent,
a second chamber wholly located above the first chamber and dimensioned to receive the article therein and configured to remove the decontamination agent that is residual on the external surfaces of the decontaminated article,
a decontamination agent supply device configured to supply the decontamination agent,
a decontamination agent control device configured to control a movement of the supplied decontamination agent,
a moving device configured to move the article placed thereon, and
an air supply and exhaust device configured to supply and exhaust clean air,
wherein:
the first chamber includes a first door dimensioned to convey the article therethrough to an inside of the first chamber from an external environment, a first supply port of the decontamination agent supply device, and an exhaust port of the air supply and exhaust device,
the second chamber includes a second door provided on a boundary with the first chamber and dimensioned to receive the article that has been decontaminated in the first chamber, a third door dimensioned to convey the article that has been aerated in the second chamber to the location outside the pass box, and a second supply port of the air supply and exhaust device,
the decontamination agent supply device is configured to convert the decontamination agent into a mist for decontamination, and to supply said mist through the first supply port inside the first chamber,
the decontamination agent control device includes vibration boards disposed adjacent to internal wall surfaces of the first chamber, wherein the vibration boards are configured to ultrasonically vibrate to generate sound flows from board surfaces in a vertical direction to press the mist supplied to the first chamber with acoustic radiation pressure thereby concentrating the mist on the external surfaces of the article,
the moving device is configured to move the decontaminated article from the first chamber to the second chamber, which is wholly located above the first chamber, through the second door, and
the air supply and exhaust device is configured to perform aeration to remove a residue of the decontamination agent from the external surfaces of the article by supplying clean air to the second chamber through the second supply port, and to discharge the air containing an aerated decontamination agent into the external environment through the exhaust port.

2. The pass box according to claim 1, wherein
the air supply and exhaust device is disposed such that the second supply port thereof is open at an upper portion of the second chamber and the exhaust port thereof is open at a lower portion of the first chamber, wherein
the pass box is configured to convert the clean air supplied from the air supply and exhaust device to the second chamber into a unidirectional flow from the upper to lower portions of the first chamber through the external surfaces of the article from the upper portion of the second chamber, and to discharge said clean air from the exhaust port that is open at the lower portion of the first chamber into the external environment while the external surfaces of the article and the inside of the first chamber are aerated when the article is in the second chamber.

3. The pass box according to claim 2, wherein
the plurality of the vibration boards is arranged to have the article in the first chamber placed therebetween and board surfaces thereof being opposite each other to primarily concentrate the resulting pressing force with the acoustic radiation pressure in a direction of the article from each of the vibration boards.

4. The pass box according to claim 3, wherein:
the decontamination agent supply device includes a mist generation means, wherein
the mist generation means is (i) a spray nozzle including a single-fluid nozzle or a two-fluid nozzle, or (ii) an ultrasonic mist generator including an ultrasonic humidifier, a nebulizer, or a piezo atomizer, and
a primary mist of the decontamination agent generated by the mist generation means is supplied to the first chamber as the mist for decontamination through the first supply port of the decontamination agent supply device included in the first chamber.

5. The pass box according to claim 4, wherein:
the decontamination agent supply device includes a mist microparticulating means, wherein
the mist microparticulating means includes one or more vibration boards configured to ultrasonically vibrate to generate sound flows from board surfaces by an ultrasound in the vertical direction,
the pass box configured to subject the primary mist of the decontamination agent generated by the mist generation means to ultrasonic vibration by the sound flows to further miniaturize the primary mist into a secondary mist, and to supply
the secondary mist to the first chamber as a miniaturized mist for decontamination through the first supply port of the decontamination agent supply device included in the first chamber.

6. The pass box according to claim 5, wherein:
the second chamber includes one or more vibration boards disposed adjacent to internal wall surfaces thereof, the vibration boards are configured to ultrasonically vibrate to generate sound flows from board surfaces by an ultrasound in the vertical direction, and to remove the decontamination agent that is residual on the surfaces of the article by passing the clean air and the sound flow in the second chamber to act on the external surfaces of the decontaminated article to be aerated.

7. The pass box according to claim 6, wherein:
the vibration board includes a base and a plurality of transmitters, wherein
transmitters from the plurality of transmitters are arranged on the planar surface of the based spatially-uniformly in transmission directions, and the transmitters are operated in the same phase, whereby
a sound flow is generated by a significantly directional ultrasound from the board surface of the vibration board in the vertical direction by mutually amplifying the ultrasounds of the plurality of transmitters in the front direction and mutually canceling out the ultrasounds of the transmitters in a lateral direction.

8. The pass box according to claim 7, configured to further miniaturize the mist for decontamination supplied to the inside of the first chamber with ultrasonic vibration generated from the vibration board.

9. The pass box according to claim 8, comprising
a control device configured to change the frequency and output of the ultrasound generated from the vibration board and/or to transmit the ultrasound intermittently to control a position or a moving speed of the mist for decontamination to concentrate said mist on the external surfaces of the article.

10. The pass box according to claim 2, wherein:
the decontamination agent control device includes a plurality of the vibration boards, wherein
the plurality of the vibration boards is arranged such that the article in the first chamber is placed therebetween and without board surfaces thereof being opposite each other, and to direct the resulting pressing force with the acoustic radiation pressure to primarily pass along a side surface of the article from each of the vibration boards, and to control
the mist for decontamination to concentrate the mist on the external surfaces of the article by moving the mist so as to rotate the mist inside the first chamber.

11. The pass box according to claim 10, wherein:
the decontamination agent supply device includes a mist generation means, wherein
the mist generation means is (i) a spray nozzle including a single-fluid nozzle or a two-fluid nozzle, or (ii) an ultrasonic mist generator including an ultrasonic humidifier, a nebulizer, or a piezo atomizer, and
a primary mist of the decontamination agent generated by the mist generation means is supplied to the first chamber as the mist for decontamination through the first supply port of the decontamination agent supply device included in the first chamber.

12. The pass box according to claim 11, wherein:
the decontamination agent supply device includes a mist microparticulating means, wherein
the mist microparticulating means includes one or more vibration boards configured to ultrasonically vibrate to generate sound flows from board surfaces by an ultrasound in the vertical direction,
the pass box configured to subject the primary mist of the decontamination agent generated by the mist generation means to ultrasonic vibration by the sound flows to further miniaturize the primary mist into a secondary mist, and to supply
the secondary mist to the first chamber as a miniaturized mist for decontamination through the first supply port of the decontamination agent supply device included in the first chamber.

13. The pass box according to claim 12, wherein:
the second chamber includes one or more vibration boards disposed adjacent to internal wall surfaces thereof, the vibration boards are configured to ultrasonically vibrate to generate sound flows from board surfaces by an ultrasound in the vertical direction, and to remove the decontamination agent that is residual on the surfaces of the article by passing the clean air and the sound flow in the second chamber to act on the external surfaces of the decontaminated article to be aerated.

14. The pass box according to claim 13, wherein:
the vibration board includes a base and a plurality of transmitters, wherein
transmitters from the plurality of transmitters are arranged on the planar surface of the based spatially-uniformly in transmission directions, and the transmitters are operated in the same phase, whereby a sound flow is generated by a significantly directional ultrasound from the board surface of the vibration board in the vertical direction by mutually amplifying the ultrasounds of the plurality of transmitters in the front direction and mutually canceling out the ultrasounds of the transmitters in a lateral direction.

15. The pass box according to claim 14, configured to further miniaturize
the mist for decontamination supplied to the inside of the first chamber ultrasonic with vibration generated from the vibration board.

16. The pass box according to claim 15, comprising
a control device configured to change the frequency and output of the ultrasound generated from the vibration board and/or to transmit the ultrasound intermittently to control a position or a moving speed of the mist for decontamination to concentrate said mist on the external surfaces of the article.

* * * * *